(12) United States Patent
Zhang et al.

(10) Patent No.: US 10,101,304 B2
(45) Date of Patent: Oct. 16, 2018

(54) PHASED ARRAY SYSTEM CAPABLE OF COMPUTING GAINS FOR NON-MEASURED CALIBRATION POINTS

(71) Applicants: Jinchi Zhang, Quebec (CA); Benoit Lepage, Quebec (CA)

(72) Inventors: Jinchi Zhang, Quebec (CA); Benoit Lepage, Quebec (CA)

( * ) Notice: Subject to any disclaimer, the term of this patent is extended or adjusted under 35 U.S.C. 154(b) by 300 days.

(21) Appl. No.: 14/753,133

(22) Filed: Jun. 29, 2015

(65) Prior Publication Data

US 2015/0377840 A1 Dec. 31, 2015

Related U.S. Application Data

(60) Provisional application No. 62/018,271, filed on Jun. 27, 2014.

(51) Int. Cl.
*G01N 29/30* (2006.01)
*G01N 29/44* (2006.01)
*G01N 29/26* (2006.01)
*G01N 29/06* (2006.01)

(52) U.S. Cl.
CPC ....... *G01N 29/4463* (2013.01); *G01N 29/069* (2013.01); *G01N 29/262* (2013.01); *G01N 29/30* (2013.01); *G01N 29/4427* (2013.01); *G01N 2291/044* (2013.01)

(58) Field of Classification Search
CPC .................................................. G01N 29/262
USPC .................................................... 73/598, 629
See application file for complete search history.

(56) References Cited

U.S. PATENT DOCUMENTS

2009/0277269 A1* 11/2009 Sarr ................ G01N 29/07
73/620
2014/0238136 A1* 8/2014 Ten Grotenhuis ............
G01N 29/0654
73/592

* cited by examiner

*Primary Examiner* — David M Gray
*Assistant Examiner* — Philip Marcus T Fadul
(74) *Attorney, Agent, or Firm* — C. Tricia Liu (57) ABSTRACT

Disclosed is a calibration method and system for non-destructive testing and inspection (NDT/NDI). The method and system involve establishment of a reference database by conducting FMC acquisition on a first calibration block having standardly known indications with a first series of depths and under a laboratory standard calibration condition. Then phased-array operation is conducted on a second calibration block, which is substantially the same as the first block, having indications with a series of corresponding user measured depths and under a second calibration condition as close to the laboratory condition as possible. The calibration is then made with the gain compensation calculated based on the response signals from the indications of the second block, the first series of gain data from the reference database, and the user measured depths for the corresponding indications under the second calibration condition.

16 Claims, 11 Drawing Sheets

PHASED ARRAY SYSTEM CAPABLE OF COMPUTING GAINS FOR NON-MEASURED CALIBRATION POINTS

CROSS-REFERENCE TO RELATED APPLICATIONS

This application claims the benefit and priority of U.S. Provisional patent application Ser. No. 62/018,271 filed Jun. 27, 2014 entitled A PHASED ARRAY SYSTEM CAPABLE OF COMPUTING GAINS FOR NON-MEASURED CALIBRATION POINTS, the entire disclosure of which is incorporated herein by reference.

FIELD OF THE INVENTION

The invention relates to an instrument for non-destructive testing and or inspection (NDT/NDI), more particularly to an improvement in the calibration of the gain compensation of a phased array (PA) ultrasound instrument utilizing full-matrix-capture of the PA data.

BACKGROUND OF THE INVENTION

During NDT/NDI testing, sound traveling through metal from an ultrasound (UT) probe goes through the process of attenuation, absorption and scattering. Flaws of identical size at different depths result in different amplitudes of sound returning to the probe. This is detrimental to quality of the UT inspection and is typically corrected either by a distance amplitude curve (DAC) or a time corrected gain (TCG). In its simplest form, a DAC is a drawing on the screen of an ultrasound instrument that accounts for the loss of sound over the sound path, which is also called the metal path because it is the path sound takes through the part being inspected, usually made of metal. DAC is a curve literally drawn on the screen either manually or digitally by the ultrasonic instrument being utilized by the NDT inspector. TCG is a correction for the DAC curve that makes the curve a straight line by automatically adjusting the gain for flaws of equal size at different sound paths (metal depths) in order that they appear visually at the same screen level on the ultrasonic inspector's screen.

For conventional UT inspection, only the TCG is required, but for Phased Array Ultrasound (PAUT), where beams have variable refraction angles (and hence different transmission coefficients), there is a need for an additional gain correction referred to as the Angle Corrected Gain (ACG). Using a combination of TCG and ACG is a common practice for PAUT inspection because it would be impossible to set every angle and sound path for a multi-transducer probe to the same sensitivity level using TCG only.

The requirement to compensate the gain for both the angle and the sound path length increases the complexity of the PAUT system calibration, which then becomes a time consuming task in the inspection process, requiring skilled and careful technicians. For example, a typical calibration sequence may involve careful scanning of several side drilled hole (SDH) defects over the full angular range at different depths in a reference calibration standard. It must be understood that PAUT is very sensitive to the coupling condition and to the probe orientation on the sample, so each of these scans involves a careful maximization of the signal at each PAUT refraction angle and depth to be used for the inspection. Another aspect to consider is the large differences in gain level required over the angular range, which typically makes it impossible to conduct the calibration scan for one depth with a single gain configuration.

A need therefore exists for a method to reduce the complexity of such a calibration for an NDI Technician in order to have a simpler PAUT calibration. More specifically, the objectives of an improvement to the PAUT calibration would be:

a. To reduce the number of acquisitions required to conduct a PAUT calibration;
b. To reduce the impact of measurement errors in the PAUT calibration process;
c. To improve the precision of the resulting gain compensation;
d. To eliminate the need for manual gain tuning to scan a defect over the full angular range of the PAUT inspection.

SUMMARY OF THE INVENTION

The invention is a method of improving the PAUT calibration process by predicting and adapting the gain compensation to be applied in the display view of the PAUT probe. The invention is based on the use of a reference calibration database acquired using the Full Matrix Capture (FMC) method in well controlled conditions, which makes it possible to reconstruct any PAUT beam configuration and generate gain compensation maps for a set of probe and wedge configurations to be included in the reference calibration database. The invention then makes it possible to adapt the predicted gain compensation to the specifics of the user configuration by taking into account different material sound velocity, different attenuation and different instrumentation sensitivity. The resulting calibration process is thus simplified from the user standpoint because it requires less user manipulation. It also tolerates user imprecisions because it uses measurements for fitting only a limited number of applicable variables instead of having the user build the whole gain map for each specific case.

DETAILED DESCRIPTION OF PREFERRED EMBODIMENT

Figures 1A, 1B:
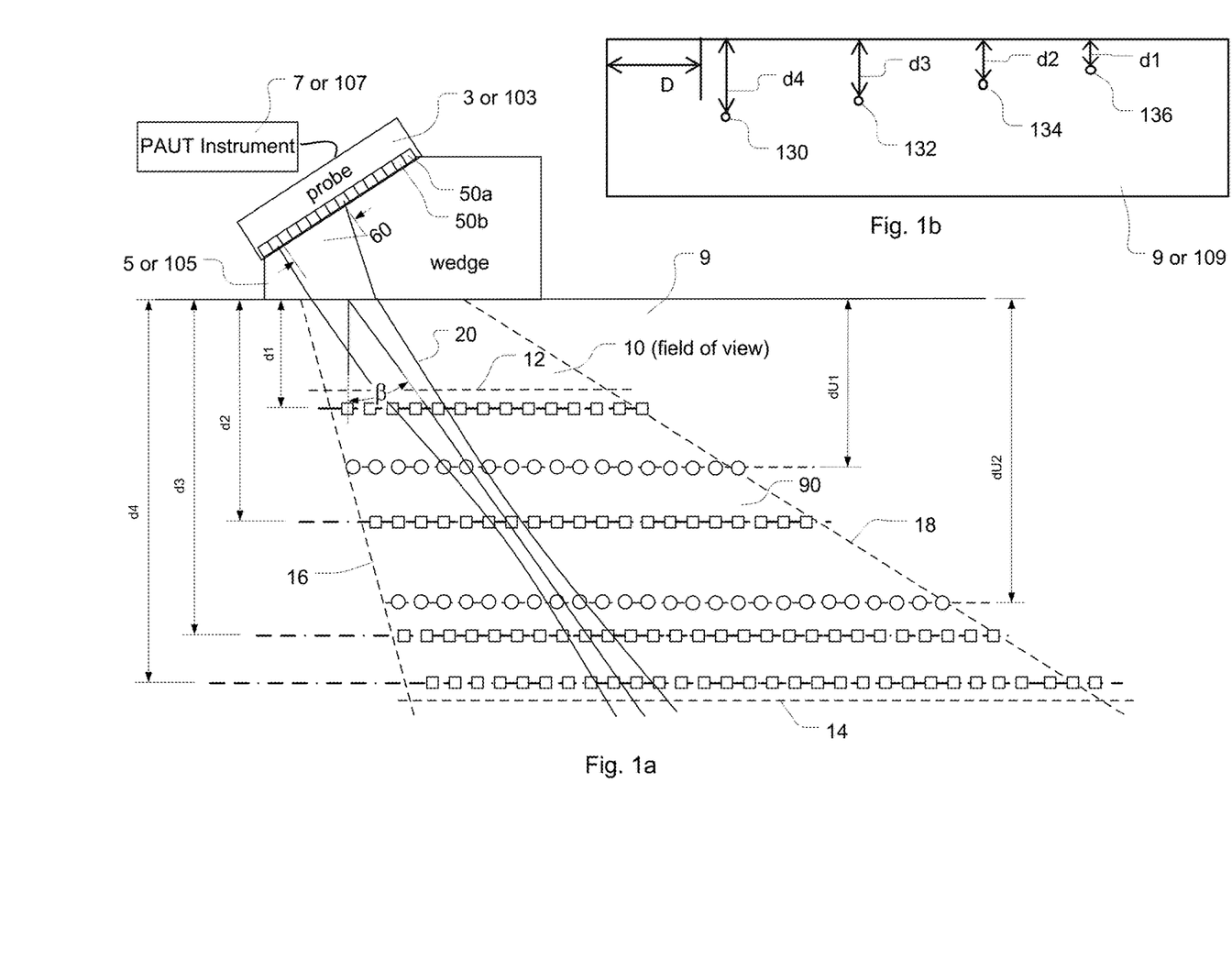
FIGS. 1a and 1b illustrate a conceptual representation of the present disclosure showing a PAUT configuration which uses a FMC database built in a lab environment, and subsequently adapts manually measured calibration points to computed calibration points covering the full field view of the inspection.

FIGS. 1a and 1b depict a conceptual representation of the present disclosure showing a PAUT configuration, and including building an off-line database, such as an FMC database. The process of populating the FMC database by obtaining ultrasonic phased array data from a standard calibration block is widely known. It usually involves use of a single axis scanner scanning a series of predetermined known indications at known depths (shown as the square legends in FIG. 1a), and obtains a series of calibration data points acquired under laboratory conditions. Also shown in FIGS. 1a and 1b is the novel aspect of the present disclosure, which is to produce computed calibration points (shown as the circle legends) covering the full field of view 10 of the inspection with those standard calibration points as well as with a limited amount of user data.

As seen in FIGS. 1a and 1b, calibration points in field of view 10 denoted by square legends are automatically generated from a previously acquired FMC database and those denoted by circle legends are measured by the user at depths dU1 and dU2, based on a simplified procedure inspired from existing practice.

A PAUT inspection configuration involving inspection elements such as a PAUT probe 3 or 103, a wedge 5 or 105, a test target material 9 or 109 is presented according to the present disclosure. For clarification, probe 3, wedge 5 and test target 9 are used collectively during user testing sessions. In comparison, probe 103, wedge 105 and reference standard block 109 are used prior to the user testing session and are a part of a reference set of configurations, which are used during the process of capturing reference calibration points and building an offline database accordingly.

PAUT parameters such as various PAUT beams 20 generated by delaying pulses to be sent to and received from each of the individual probe elements, such as 50a and 50b comprised in an active aperture 60, results in the field of view of the PAUT probe. In order to conduct a reliable PAUT inspection, the correlation between a defect of a given size and the signal amplitude of the PAUT measurement should be known and compensated at least in the portion of the field of view 10 to be used for the inspection and defined as an inspection plane 90. Inspection plane 90 is typically delimited by minimum 12 and maximum 14 depths as well as minimum 16 and maximum 18 refraction angles β.

Typically, referring to FIG. 1b, reference standard 109, with material similar to 9 and including multiple side drilled holes (SDH) at multiple known depths, is used to establish the correlation between the SDH in reference standard 109 and the responses of probe 103 in the inspection configuration. Building this correlation is relatively tedious in existing practice since it is necessary to accurately scan the SDH at multiple depths (for example d1, d2, d3 and d4) within the full field of view to be used for the inspection in order to reach the desired precision. Further complicating the task is the fact that differences in sensitivity over the angular and depth range are such that multiple manipulations of the instrument PAUT gain are needed in order to complete the process. Another limitation of the existing calibration process is the precision of the data acquired by the user. An imprecision of about 2-3 dB is typically induced by the manual manipulation of the probe, which directly impacts the precision of the compensation to be applied to the instrument.

The objective of the present disclosure is to provide a means to accurately calibrate the whole inspection plane using a limited set of user measurements. This is preferably achieved in the present disclosure by utilizing a database of measurements previously acquired at depths d1, d2, d3 and d4 in well controlled conditions, and by adapting those measurements to a limited set of readings acquired manually by the user at depths dU1 and/or dU2.

Figure 2:
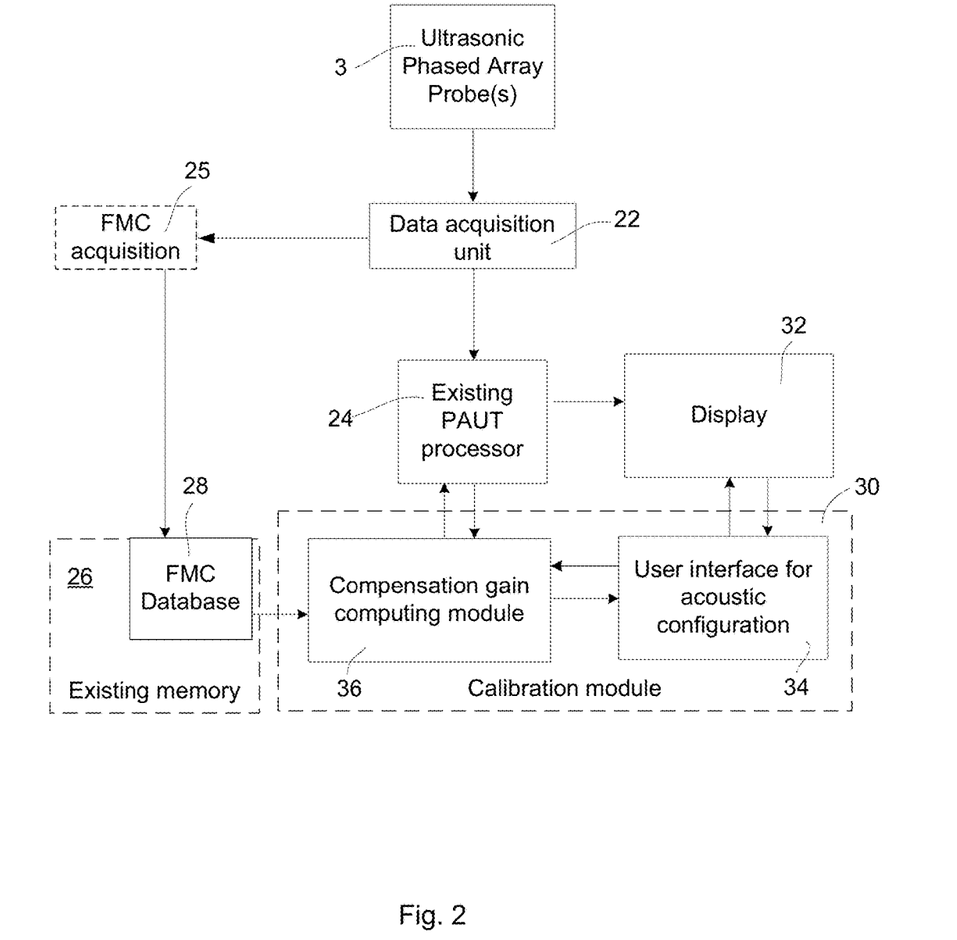
FIG. 2 is a schematic view of phased array instrument gain calibration calculated for full scan range and varied wedge-influenced combinations according to the present disclosure.

Reference is now made to FIG. 2, which depicts a PAUT system according to the present disclosure. This system achieves improved calibration capability by intelligently computing fuller calibration points with the use of a database, such as a full matrix capture (FMC) database. The approach presented by the system is advantageous because it allows accurate replacement of some calibration points which were previously manually captured, saving many man-hours in the process.

As shown in FIG. 2, the system comprises an ultrasonic phased array probe 3, a data acquisition unit 22, an existing data processing unit 24, a memory 26 which further includes an FMC database 28 and an intelligently extended calibration module 30. An FMC data acquisition unit 25, which can either be from another phased array device or from the same phased array system (herein defined as data acquisition unit 22), is used for the FMC data capture operation. It should be noted that FMC phased array data acquisition on standard reference blocks is a known practice to those skilled in the art.

Calibration module 30 further comprises a user interface (UI) module 34 for making calibration and/or general testing related user input for acoustic configurations, and a compensation gain computing module 36. Alternatively, gain computing module 36, UI 34 and the existing PAUT processor can together compose a new data processing unit (not shown) when the method of the present disclosure is used for a newly designed PAUT, versus being added to an existing PAUT system.

It should be understood that a database 28 of reference measurements can be acquired with considerable improvement in stability and reproducibility by using an automated scanner seen in existing practice for laboratory experiments, which applies constant pressure and maintains nearly perfect probe and wedge alignment relative to reference block 109. A full matrix database is preferably built by using existing database technique. Then reference measurements are preferably acquired using the Full Matrix Capture (FMC) acquisition scheme using an appropriate acquisition unit 25. The data resulting from FMC acquisition schemes has been demonstrated to allow post-processing reconstruction of any PAUT beam in existing practice, as detailed for example in the publication *Post-processing of the Full Matrix Of Ultrasonic Transmit-Receive Array Data For Non-Destructive Evaluation* by Caroline Holmes, Bruce W. Drinkwater, and Paul D. Wilcox (NDT & E International, Volume 38, Issue 8, December 2005, pp. 701-711). Multiple acquisitions of data from reference block 109 are made by iteratively varying the probe position D (typically with a resolution smaller than 0.5 mm) in order to completely record the relationship between probe 20 and the multiple SDHs (130, 132, 134 and 136) shown in FIG. 1b and located at depths d1, d2, d3 and d4 respectively.

It should be noted that such reference measurements are preferably carried out in a laboratory environment under controlled conditions, and the FMC acquisition is performed prior to the actual testing sessions.

It should be understood that reference probe 103 and wedge 105 are the same model as the user's probe 3 and wedge 5. Even though they are not perfectly identical to the user's counterpart, they share the same physical and geometrical characteristics. Therefore potential differences between the reference and user probe and wedge configurations could be associated mainly with differences in elementary sensitivity patterns, wedge wear, probe coupling and similar factors. As for reference material 109, it is assumed that the differences between this block and user's material 9 include different attenuation and slightly different material sound wave velocity; both materials have a similar density and are assumed to be isotropic for the exemplary case of the present disclosure.

In order to provide guidance for reading, the method of attaining calibration points in the inspection plane with minimum manual acquisition and with optimized calibration gain is further described in FIGS. 3a~8. In FIGS. 3a~6b, a method of "predicting" or calculating fuller points of calibration based on a full-matrix database together with other manually measured calibration points is described. In FIGS. 7a~9b, a method of optimizing the calibration gains for those predicted calibrations is described. It should be noted that the order in which the figures are organized herein is for the purpose of providing clear illustration, and that different orders of these figures are within the scope of the present disclosure.

Figure 3A:
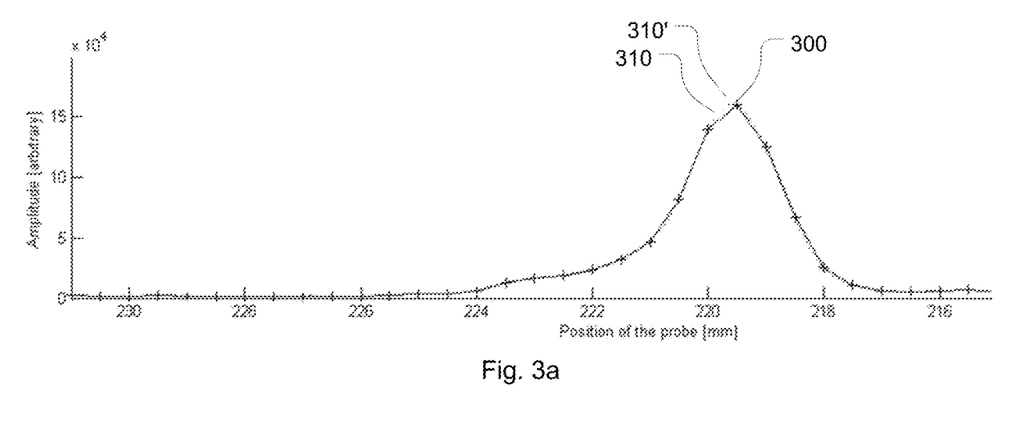
FIGS. 3a and 3b are charts illustrating the process involved in defining the amplitude of the response at various angles according to the present disclosure.
Figure 3B:
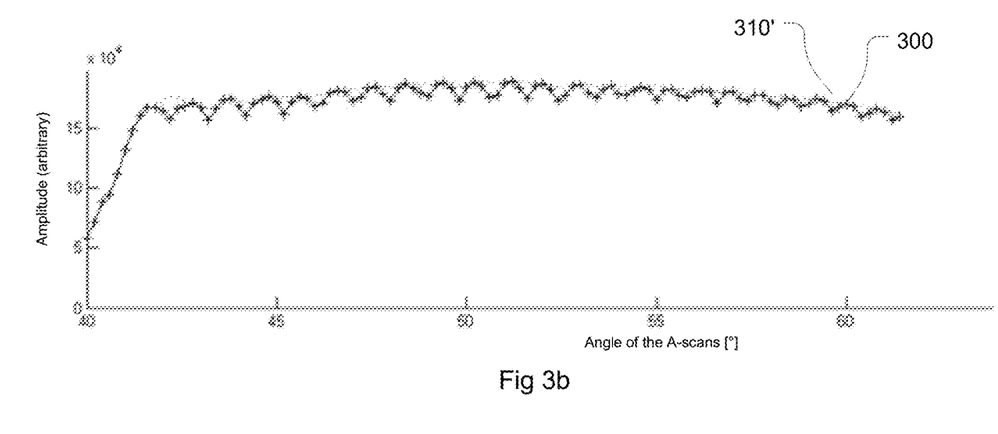

With continuing reference to FIGS. 1a, 1b and 2, and referring primarily now to FIGS. 3a and 3b, the figures show how FMC database 28 is used to predict the PAUT response with a given PAUT configuration of aperture, refraction angle range and focalization. FIG. 3a illustrates, for exemplary SDH 132, the amplitude obtained by recombination of FMC database 28 at various positions D for a PAUT aperture of 32 elements, a focalization of 25 mm and a refraction angle of 60 degrees. FIG. 3a is a plot of the amplitude of ultrasonic echo signal versus probe position. FIG. 3b is a plot of the amplitude of ultrasonic echo signal versus scan angles. Of particular interest in FIG. 3a is the experimental maximum (peak) 300 obtained when the probe is at 220.5 mm from the edge of the bloc. This maximum is then reported on FIG. 3b which illustrates the maximum obtained for the SDH 132 at various refraction angles. Note that, by using known curve-fitting methods, the precision of the curve in FIG. 3b can be further improved by fitting a continuous curve 310 in FIG. 3a, which defines a new maximum value 310' to be used for smoothing the FIG. 3b curve.

Figure 4A:
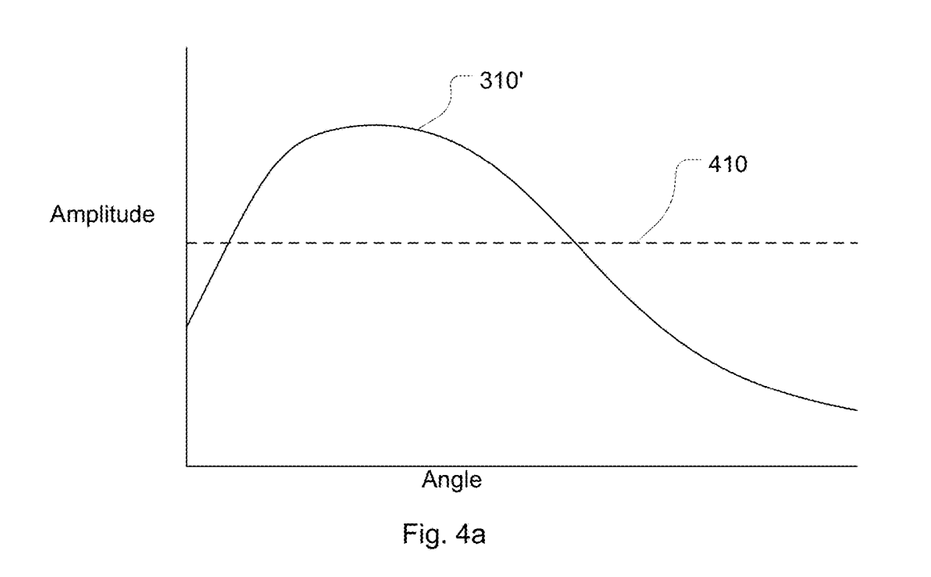
FIGS. 4a and 4b are charts that illustrate the conversion from an amplitude measurement to gain compensation according to the present disclosure.
Figure 4B:
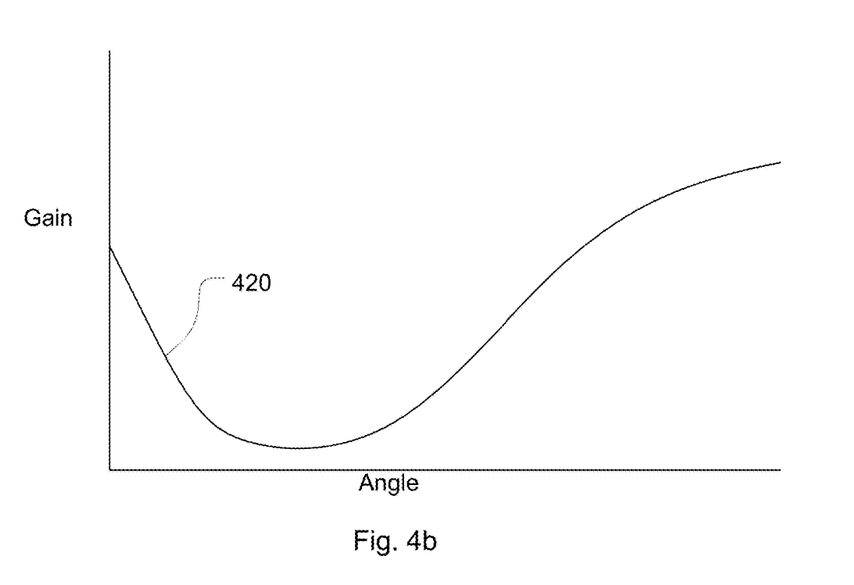

The process of converting measurements obtained in FIGS. 3a and 3b to gain compensation is illustrated in FIGS. 4a and 4b. The measured 310' and target 410 amplitude level for the inspection are schematically shown in FIG. 4a, while the gain 420 required to reach the target is shown in FIG. 4b. The gain curve of FIG. 4b is built using the following relationship:

$$\text{Gain (dB)} = 20*\log(\text{Amplitude\_target}/\text{Amplitude\_measured}) \quad \text{Eq. 1}$$

wherein a gain versus angle curve such as that shown in FIG. 4b is in common use among those skilled in the art for data acquired using a PAUT instrument, and is referred to as angle corrected gain (ACG).

Figure 5:
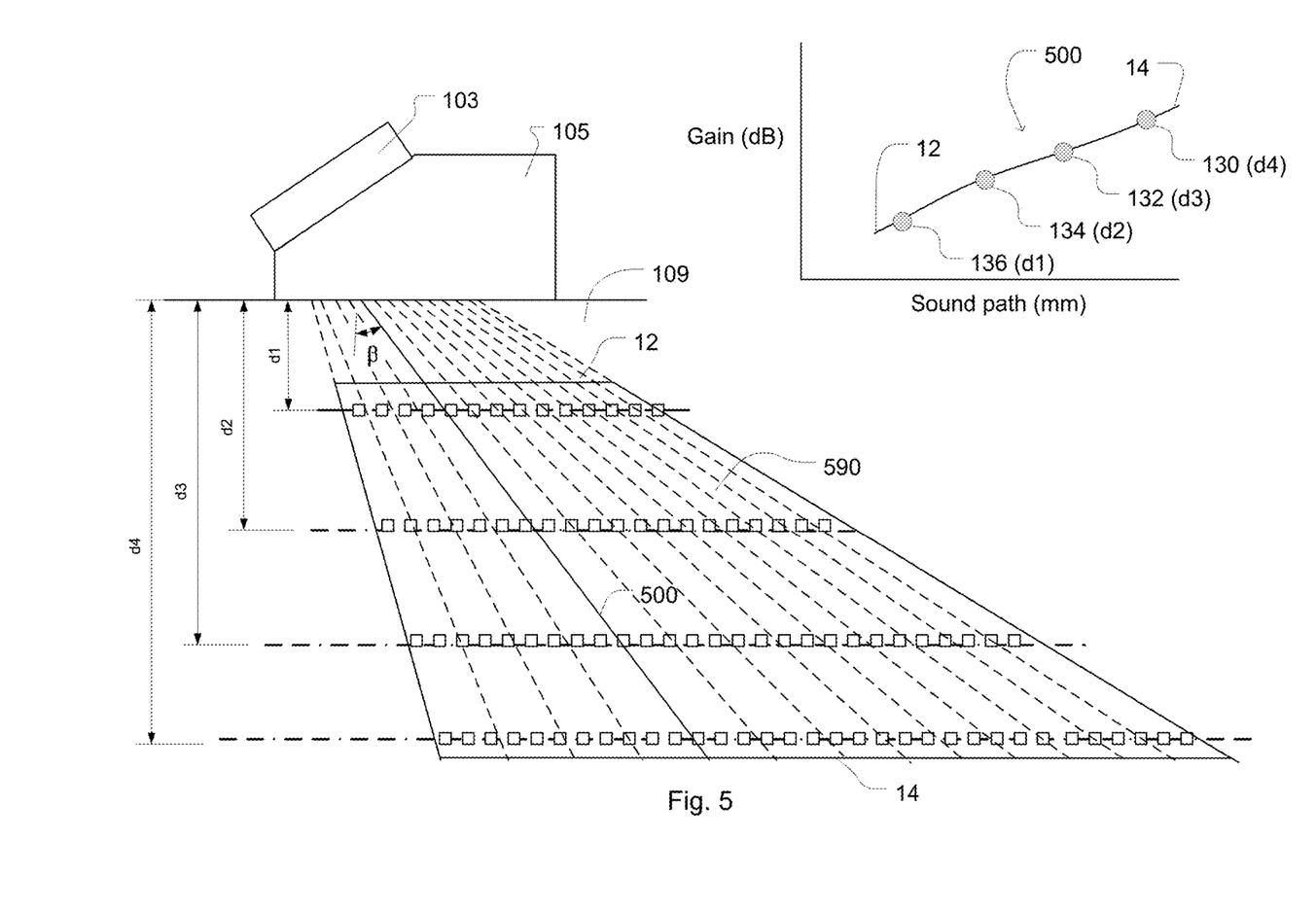
FIG. 5 is a representation of the DACG in relation to the probe's field of view.

Referring to FIG. 5, the last step in building the gain correction for an entire inspection plane 590 for the reference measurement is illustrated. In this case, for each relevant refraction angle, a curve such as 500 corresponding to the sound path (SP) through the inspected part versus the required gain is interpolated using the multiple measurements made on SDH 130, 132, 134 and 136 on reference material 109. Curve 500 is bounded by minimum and maximum depth 12 and 14 defining inspection plane 590. The compensation gain is thus known for any refraction angle and SP on the reference sample and will be referred to herein as the reference Distance and Angular Compensated Gain (r-DACG). The r-DACG is expressed as a gain matrix which is bi-dimensional in the β and SP axes, where β is the refraction angle and SP the sound path in the inspected material (distance in mm).

Figures 6A, 6B:
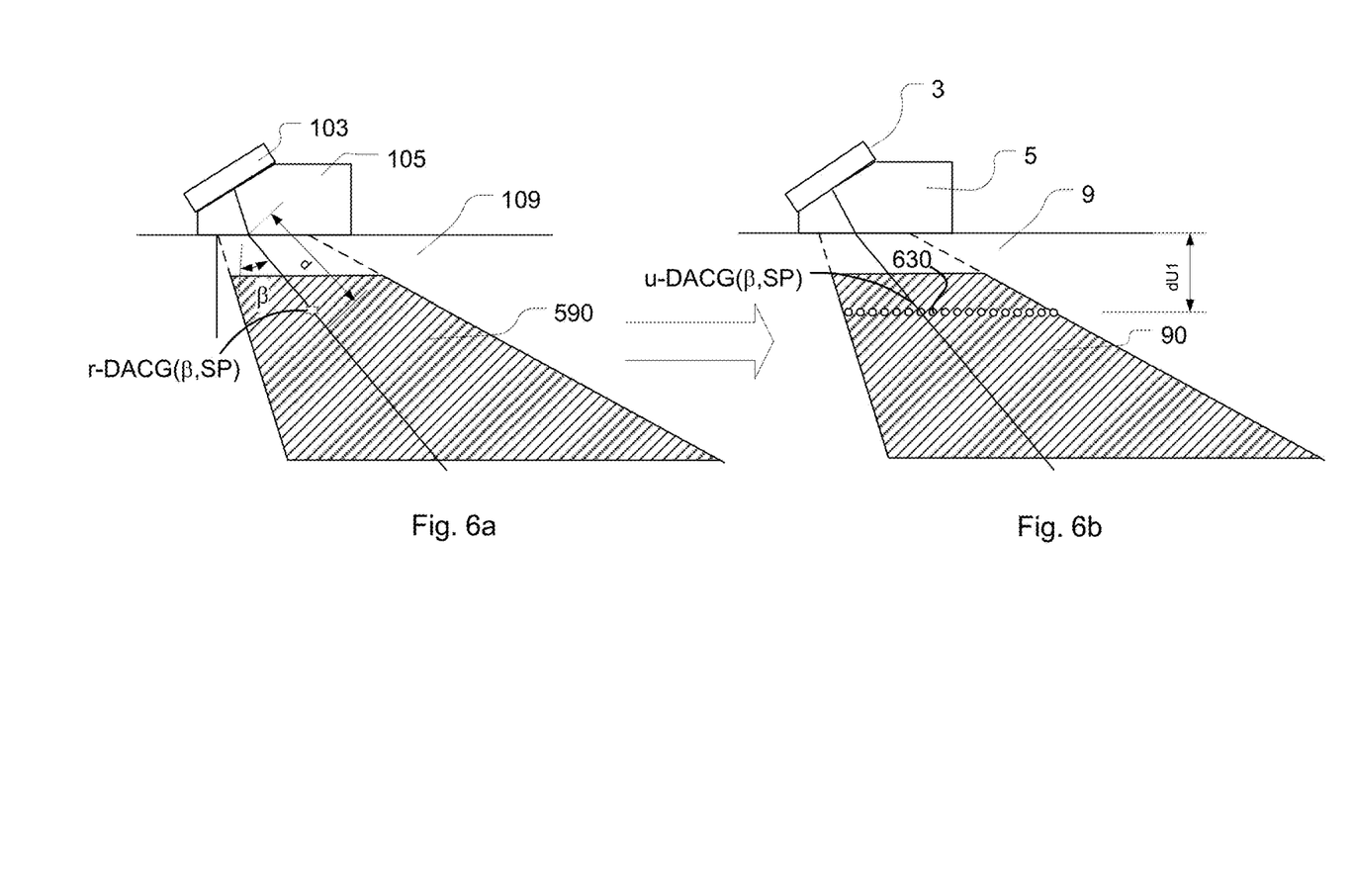
FIGS. 6a and 6b illustrate the transposition of the r-DACG to the u-DACG.

Reference is now made to FIGS. 6a and 6b. Having r-DACG, it is now desirable to use it for predicting the user Distance and Angular Compensated Gain (u-DACG) on the test target 9 as shown in FIG. 6b. FIG. 6a is a representation of the reference measurement achieving r-DACG on reference standard 109 as described above. FIG. 6b is a representation of field testing on test object 9. For purpose of illustration, we assume that the sound velocities of both reference 109 and test target 9 are known at this step of the process, which makes it possible to express the DACG in terms of β and SP. (Known methods exist to measure the sound velocity of a material, and details of these velocity measurements of are thus outside the scope of the invention). As illustrated in FIGS. 6a and 6b, as a first estimate which neglects the global sensitivity difference, the r-DACG is directly copied to u-DACG. This operation is a good first approximation because the DACG are expressed in a format (β and SP) that already accounts for sound velocity variation in the inspected material itself.

There are still some remaining signal variations resulting from the use of different material sound velocities in reference sample 109 relative to test target 9; the most important source of error is expected to be the differences in transmission coefficient at the interface of wedges (105, 5) and parts (109, 9). To illustrate the impact of a sound velocity difference between 109 and 9, the transmission coefficient ratio between test target 9 and reference material 109 has been plotted (FIG. 7a) for various refraction angles ranging from 40 to 70 degrees (representative of most angle beam inspections), and for a user material having sound velocities different from the reference carbon steel block shear wave (SW) velocity of 3230 m/sec and longitudinal wave velocity of 5900 m/sec.

Figure 7A:
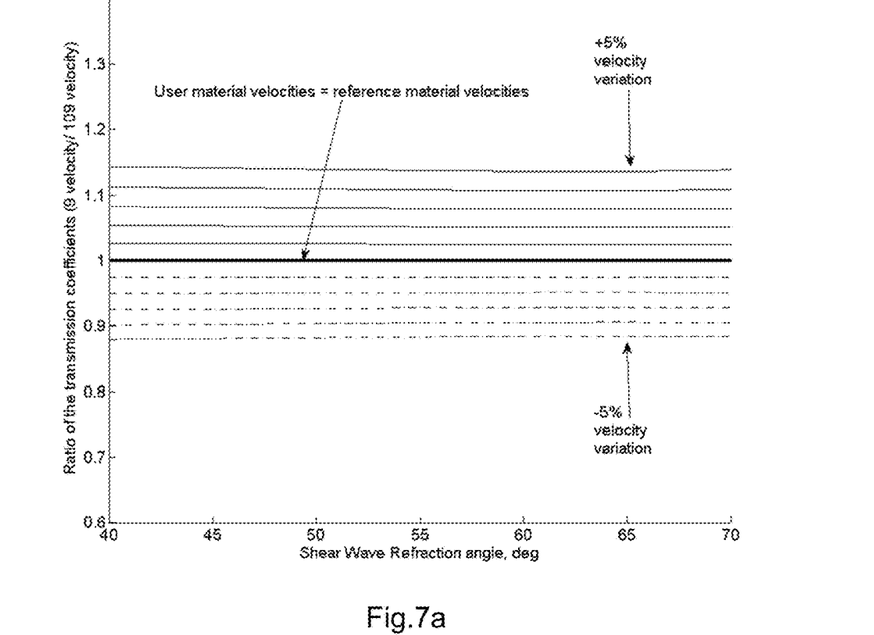
FIGS. 7a and 7b illustrate the impact of user material sound speed relative to the reference material sound speed.
Figure 7B:
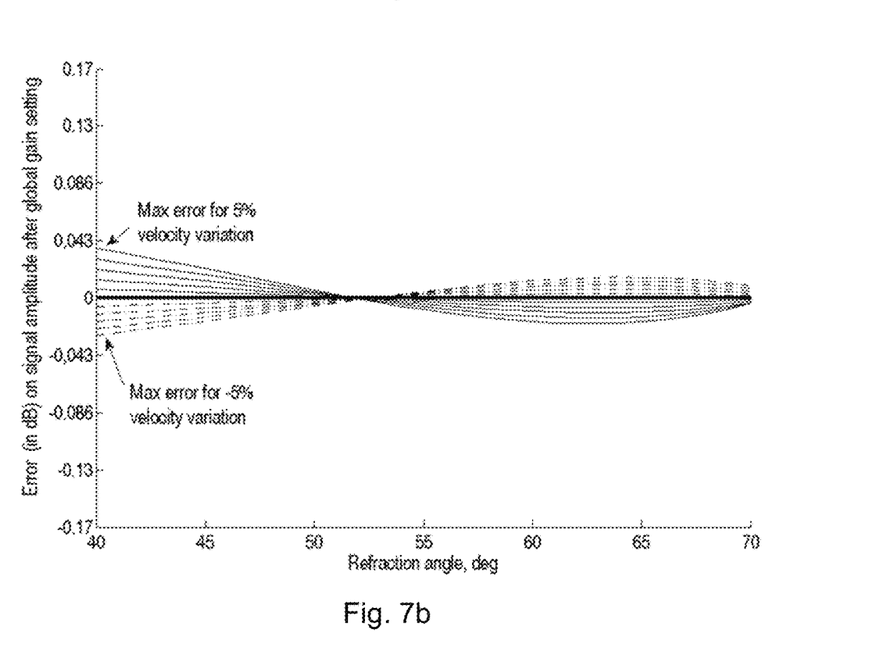

As can be seen in FIG. 7a, the ratio of transmission coefficients equals 1 when user material velocity equals reference material velocity. The ratio increases above one or decreases below one when velocity variation increases or decreases, up to +5% or down to −5%, respectively. However, since the various curves for different velocity are almost parallel to each other, most of the variation in transmission coefficients can be compensated with global gain tuning FIG. 7b illustrates the error (in dB) in signal amplitude after the global gain tuning; the 0.04 dB maximum error associated with a ±5% variation of material velocity confirms the utility of the invention for a range of materials with different sound wave velocities. Note that the 0.04 dB error in FIG. 7b is orders of magnitude below the typical +/−2 dB repeatability target for ultrasonic calibration.

It should be noted that longitudinal plane waves propagating in a wedge undergo mode-conversion at the interface with the test material, and continue to propagate in part as vertically-polarized shear (SW) waves. For reference, the general expression for the transmission coefficient of SW waves can be found, for example, in a book publication *Ultrasonic Nondestructive Evaluation Systems Models and Measurements*, by Lester W. Schmerr Jr. and Sung-Jin Song (2007), Springer, pages 518-519. Calculations leading to the generation of FIGS. 7a and 7b are derived from this reference, assuming a round trip between the probe and the inspected part.

Returning to FIGS. 6a and 6b, having a first predicted u-DACG for test target 9 sound velocity, this u-DACG applied on the PAUT instrument 7 makes it possible to obtain an initial set of user measurements on a SDH 630 at depth dU1. Typically, a manual gain setting can be applied to compensate for cable length attenuation, probe sensitivity and/or for some differences in material sound velocity, provided that this gain is uniformly applied at all angles. At this point, the predicted u-DACG is useful to facilitate the acquisition of SDH 630 reference data and to compensate for the important differences in signal strength over the angular range (and thus directly achieving one of the objectives of this invention).

Figure 9A:
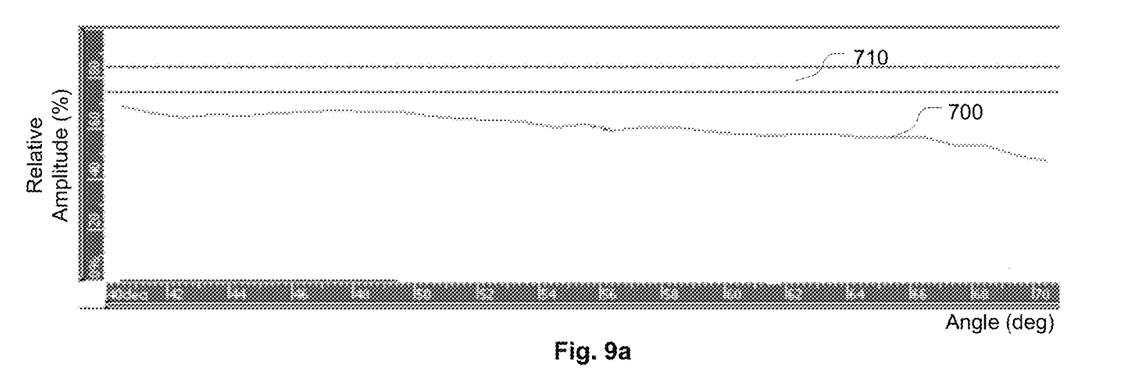
FIGS. 9a and 9b show the effect of attenuation compensation on the resulting calibration signal.
Figure 9B:
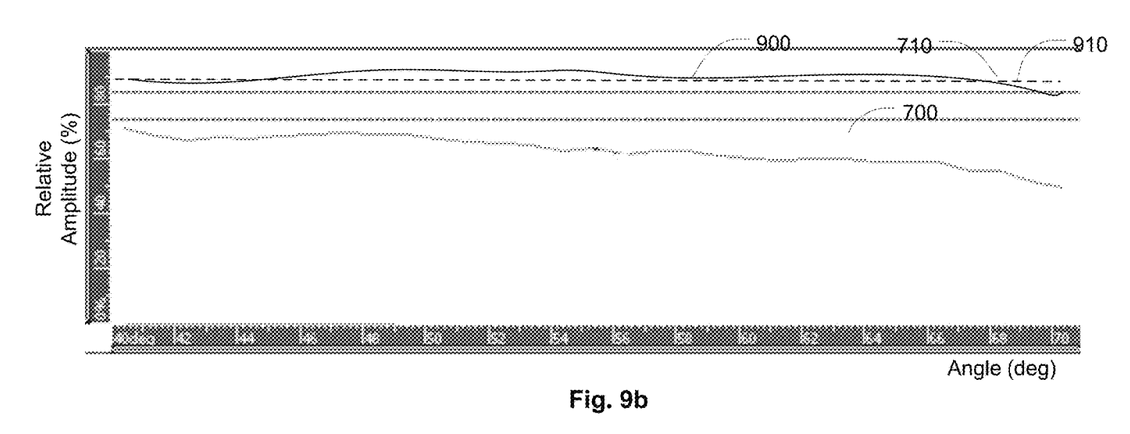

FIGS. 9a and 9b illustrate the typical acquisition of an amplitude envelope 700 on a SDH such as 630 after the application of the predicted u-DACG. Typically, our objective for the instrument calibration is to bring envelope 700 within a given tolerance 710 (for example, ±5%) at the 80% amplitude level. As illustrated in FIG. 9a, although the u-DACG brings the signal close to the 710 zone, there is still a gap to compensate which is mainly caused by differences in material attenuation from 9 to 109 and global sensitivity differences between the user instrumentation (including probe 3, wedge 5, PAUT instrument 24, SDH size and the round trip transmission coefficient for material 9) and their reference counterparts 103, 105, 107 and 109.

Figure 8:
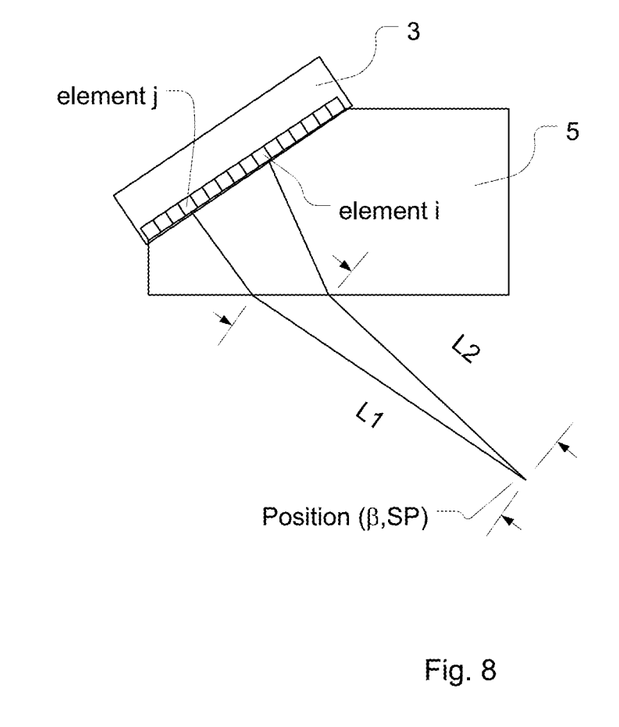
FIG. 8 illustrates the sound path involved in material attenuation for an FMC A-scan.

Referring now to FIG. 8, in order to account for the different PAUT signal attenuation in user material 9, the original FMC elementary A-scan data should be modified. It should be understood by those skilled in the art that, the time-based calibration matrix corresponding to each interaction between a transmitter element and a receiver element in the PAUT probe can be modified. FIG. 8 shows the ultrasonic path associated with the generation of a pulse at element i and its reception by another element j in relation to a position ($\beta$, SP) in the inspection plane. The length of the ultrasonic path affected by the variation of attenuation is defined by:

$$L(\beta, SP) = L_1(\beta_{L1}, SP_{L1}) + L_2(\beta_{L2}, SP_{L2}),$$

where L1 is the sound path from element i to the indication; L2 is the sound path back from the indication to element j. Therefore the modification of the original A-scan of the FMC acquisition database can be expressed as:

$$S_c(i,j,L) = S_0(i,j,L) * e^{-F*L} \qquad \text{Eq. 2}$$

where, $S_0(i,j,L)$ is the original FMC signal for the element combination (i,j) and total path length in the target material L;

F is the difference in attenuation factor between reference 109 and user material 9;

$S_c(i,j,L)$ is the corrected FMC signal data that takes into consideration the user's material attenuation factor.

$L_1$ and $L_2$ are the sound paths from element i to element j via the indication.

By using corrected FMC signal data as defined by Eq. 2, we can generate a u-DACG' at depth dU1 with different material attenuation in order to compensate for the difference between the testing material and the reference material. The effect of the different attenuation can be seen in FIGS. 9a and 9b as the displacement of envelope 700 relative to the target zone 710. Envelope 700 is obtained by applying u-DACG on PAUT data acquired manually by the user on his block 9, and by isolating the amplitude maxima obtained at each steering angle. In FIGS. 9a and 9b, amplitudes are expressed as % of the full range amplitude (a common practice in Ultrasonic Non-Destructive testing). Target zone 710 is defined here as the acceptable range of amplitude variation for envelope 700 on the reference defect. As illustrated in FIGS. 9a and 9b, fitting envelope 700 to target zone 710 can be done iteratively by finding a combination of global gain and attenuation which brings the original envelope 700 within the target zone 710, and minimizes the variation between a corrected envelope 900 and a center 910 (shown as a dashed line) of target zone 710. Using the resulting attenuation and gain settings the u-DACG' can be generated for the full user inspection plane 90.

It can be appreciated by those skilled in the art that, although we have described generation of a u-DACG' using reference envelope 700 acquired at a single depth dU1, the process is fully compatible with acquisition of user data at two or even more depths. Obtaining more user data would result in better precision for the u-DACG'.

It must also be understood that the reference FMC database 28 can include more or less than the four different defect depths d1, d2, d3, d4 described in this specification, as the invention is fully flexible on this aspect. Again, having more reference data would result in improved precision.

Figure 10:
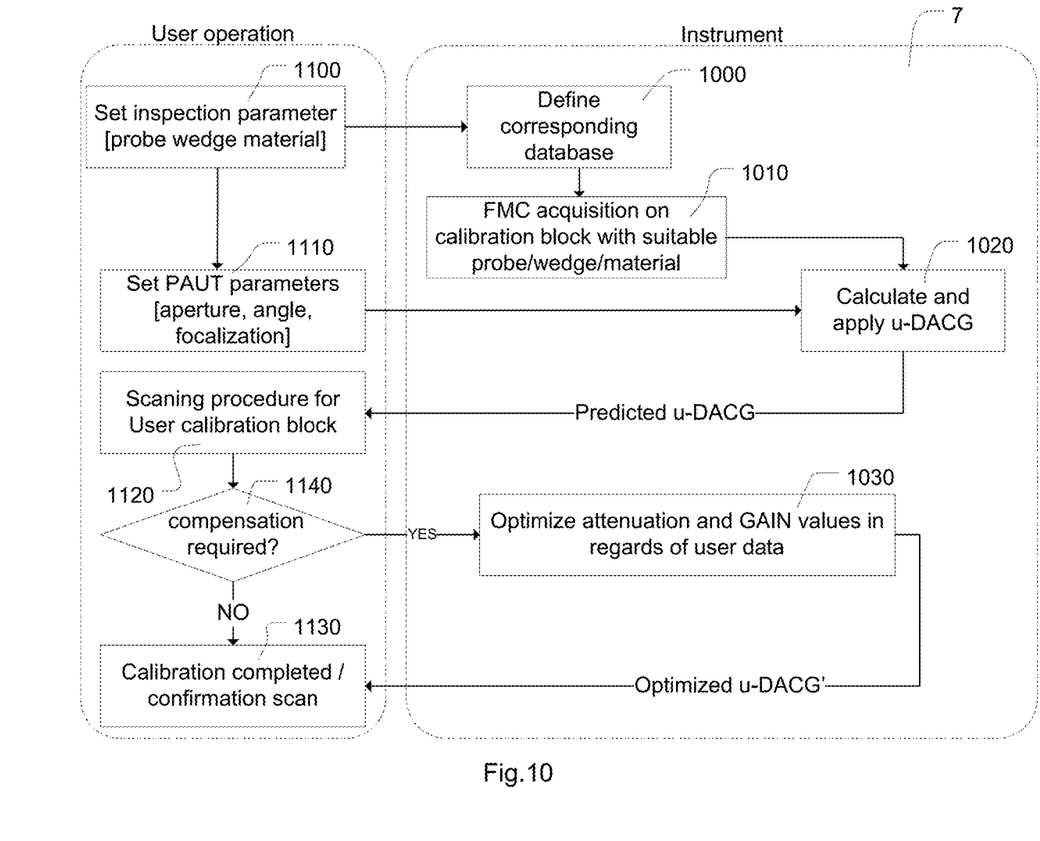
FIG. 10 is a block diagram illustrating the calibration process of the invention.

Reference is now made to FIG. 10, which schematically summarizes the use and the process of carrying out the method disclosed in the present invention. The flow chart diagram of FIG. 10 includes two parts: the first part on the left side shows steps involving user operation, which are executed mostly via user interface 34 in FIG. 2; the second part on the right side shows processes executed by the instrument 7. In step 1100, the user defines the inspection parameters, including the probe model, the wedge model and the inspected material sound velocity. In step 1000, PAUT instrument 7 sorts through the available FMC acquisition databases 28 to find the most suitable one for the inspection. In 1110, the user must define the PAUT parameters to be used for the inspection, including aperture, angular range and focalization; those parameters are transmitted to step 1020 in which the instrument calculates the predicted u-DACG from the PAUT parameters of 1110 and the selected FMC acquisition database 28, according to the method described in the present disclosure. It should be noted that the principles and details involved in predicting the u-DACG, as carried out in step 1020, are explained in full in the descriptions associated with FIGS. 3~6.

In step 1120, the user scans the calibration block (test target) of material 9, and determines if the predefined u-DACG is suitable or not based on the initial amplitude envelope 700 obtained, as shown in FIG. 9b. If required, the instrument can automatically compensate the gain and attenuation in step 1030 to bring corrected envelope 900 as close as possible to target 910 by defining an optimized u-DACG' that makes it possible to complete the calibration within target zone 710 in step 1130.

Figure 11:
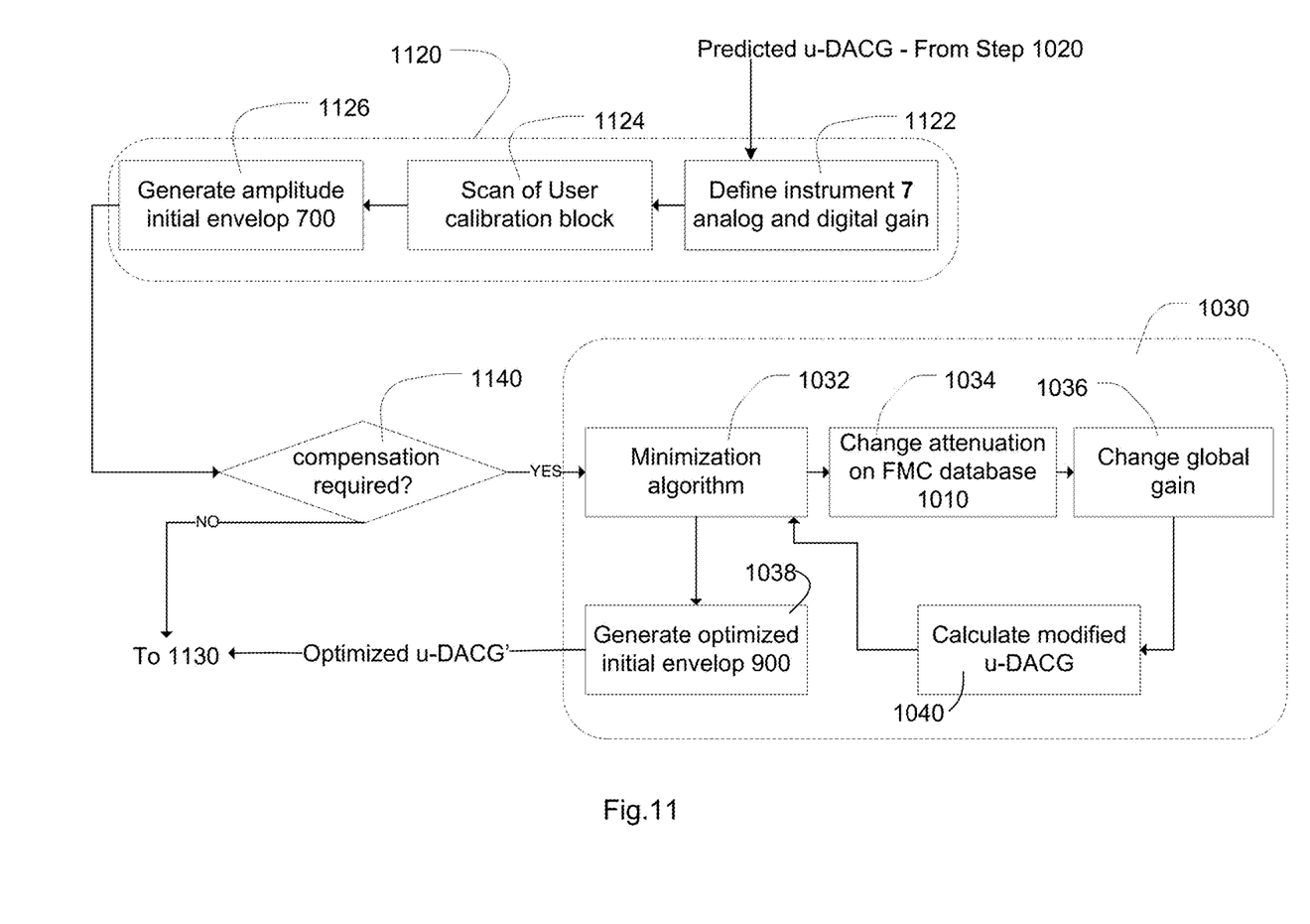
FIG. 11 is a more detailed representation of the optimization process which compensates for variations in attenuation and global gain.

Further details of the processes in steps 1120 and 1030 are provided in FIG. 11. In step 1122, the invention includes the ability to define and apply DACG related analog and digital gain to the PAUT instrument 7, based on the predicted u-DACG. User modification of the global gain in step 1122 allows precise measurement of the user calibration sample in 1124. In step 1126, the initial envelope 700 is directly generated from the acquired data and, based on the variance between envelope 700 and target zone 710, the user defines in 1140 whether or not automatic attenuation and gain compensation are required. If the user asks for automatic compensation, a minimization algorithm in step 1032 processes the effect of changing attenuation in 1034 and global gain in 1036 through calculation of modified u-DACG in 1040. The minimization algorithm iteratively changes attenuation and global gain settings to minimize the difference between target envelope center 910 and corrected envelope 900. Upon completion of optimization process 1032, a new envelope 900 can be generated and displayed to the user.

It should be noted that the principles and method previously explained with reference to FIGS. 7~9b are summarized and executed in step 1030 and its sub-steps, as shown in FIG. 11.

It should also be noted that the method taught in the present disclosure can be implemented or executed in steps organized in many ways. The flow charts of steps in FIGS. 10 and 11 are only meant to show exemplary ways of performing the presently disclosed method, and should not be construed in any way as restricting the scope of the presently disclosed method.

It should further be noted that the PAUT system with the improved calibration method can take many alternative forms. For example, the process of building the FMC database on a standard block can be done by a separate calibration PA instrument, different from that of the testing instrument as shown in FIG. 1a, or it can be done by using the same instrument as the testing instrument. It should be understood that all variations of this nature are within the scope of the present disclosure.

What is claimed is:

1. A non-destructive testing and inspection (NDT/NDI) system operable to conduct an NDT/NDI calibration and a test operation, a first calibration to be performed on a first calibration block made of a reference material and having standardly known first indications with a first series of known depths and under a first calibration condition, and a second calibration to be performed on a second calibration block made of a test material and having second indications with a second series of known depths and under a second calibration condition, wherein the test operation is to be performed on a test object made of the test material,
the NDT/NDI system comprising:
at least one phased array probe operable to beam ultrasonic energy into the calibration blocks and the test object, receive response echoes and provide corresponding sets of electronic echo signals as response signals;
a data acquisition unit configured for receiving the electronic echo signals from the at least one probe and sending commands to the probe;
a reference database containing a first series of reference data prepared by conducting a phased array full-matrix-capture (FMC) scanning operation on the first indications of the first calibration block;
a data processing and analyzing unit which is configured to process and analyze the electronic echo signals, and which further comprises a compensation gain computing module configured to compute gains for calibration applied to the response signals, the computation of the gains being based on the first series of reference data from the reference database, the second series of known depths of the second calibration block for the corresponding indications of the first series of known depths and the second calibration; and,
wherein the compensation gain computing module further comprises a gain optimizing module configured to generate distance angle corrected gain (u-DACG) or time corrected gain (u-TCG) values, and to compensate the u-DACG values based on the differences between the first and the second calibrations, the compensation being calculated according to the equation, $$S_c(i,j,L) = S_0(i,j,L) * e^{-F*L}$$

wherein,
$S_0(i,j,L)$ is a reference amplitude on a data cell of the reference database corresponding to a transmitting probe element i and a receiving probe element j,
L is a total sound path length in the first calibration block corresponding to the transmitting probe element i and the receiving probe element j,
F is an attenuation factor difference due to a sound velocity difference between the first calibration block and the second calibration block, and,
$S_c(i,j,L)$ is a corrected amplitude of the data cell, taking into consideration the attenuation factor difference.

2. The NDT/NDI system of claim 1, wherein the data acquisition unit and the data processing and analyzing unit compose a part of a first phased array inspection device.

3. The NDT/NDI system of claim 2, wherein the first phased array inspection device further comprises an electronic memory and the database can be transferred to and/or stored in the memory.

4. The NDT/NDI system of claim 2, wherein the reference data is obtained by using a second phased array inspection device for preparing the reference database on the indications of the first block.

5. The NDT/NDI system of claim 1, wherein the reference database containing the reference data is obtained on the indications of the first block in a session prior to the test operation, in a laboratory environment, with known ambient conditions, and the first block is a standard testing block.

6. The NDT/NDI system of claim 1, wherein the first calibration block is a standard calibration block, and the second calibration block is a user calibration block.

7. The NDT/NDI system of claim 1, wherein the first calibration is performed with a first wedge and a first probe and the test operation is performed with a test wedge and a test probe, wherein the first probe is a same probe model as the test probe, wherein the first wedge is a same wedge model as the test wedge, and wherein a sound velocity in the reference material is greater than 95% and less than 105% of a sound velocity in the test material.

8. The NDT/NDI system of claim 1, wherein the system generates reference distance angle corrected gains (r-DACG) based on the reference data obtained from the first indications.

9. The NDT/NDI system of claim 8, wherein the compensation gain computing module further comprises a u-DACG Prediction module for generating the u-DACG or u-TCG curves.

10. The NDT/NDI system of claim 9, wherein the u-DACG Prediction module, is configured to use curve fitting and interpolation for generating the u-DACG.

11. The NDT/NDI system of claim 7, wherein the gain optimizing module is configured to perform an automatic minimization process, in which it iteratively varies attenuation and global gain settings from the first series of gain data to minimize the difference between a target data envelope and a corrected data envelope, wherein the target data envelope is a desired data display zone.

12. A method of conducting a calibration and a test operation for a non-destructive testing and inspection (NDT/NDI) system, the system including at least one phased array ultrasonic probe, a data acquisition unit, a data processing and analyzing unit, a first calibration block made of a reference material and having known first indications with a first series of known depths, and a second calibration to be performed on a second calibration block made of a test material and having second indications with a second series of known depths, wherein the test operation is to be performed on a test object made of the test material, the method comprising the steps of:

firing the at least one phased array probe operable to beam ultrasonic energy into the first calibration block, receiving response echoes and providing corresponding sets of electronic echo signals which are response signals, receiving the electronic echo signals via the data acquisition unit from the at least one probe and sending transmit commands to the probe;

building a reference database containing reference data prepared by conducting a phased array full-matrix-capture (FMC) operation of the steps of firing and receiving on the first indications, computing gains applied to the response signals, based on the first series of gain data from the reference database, the second series of known depths of the second calibration block for the corresponding indications of the first series of known depths and the second calibration; and, generating distance angle corrected gain (u-DACG) or time corrected gain (u-TCG) values and compensating the u-DACG values based on the differences between the first and the second calibrations, the compensation being calculated according to the equation, $$S_c(i,j,L) = S_0(i,j,L) * e^{-F*L}$$

wherein, $S_0(i,j,L)$ is a reference amplitude on a data cell of the reference database corresponding to a transmitting probe element i and a receiving probe element j, L is a total sound path length in the first calibration block corresponding to the transmitting probe element i and the receiving probe element j, F is an attenuation factor difference due to a sound velocity difference between the first calibration block and the second calibration block, and, $S_c(i,j,L)$ is a corrected amplitude of the data cell, taking into consideration the attenuation factor difference.

13. The method of claim 12, wherein the data acquisition unit and the data processing and analyzing unit compose a part of a first phased array inspection device.

14. The method of claim 13, wherein the reference data is obtained by using a second phased array inspection device for preparing the reference database from the first indications.

15. The method of claim 12, wherein the first phased array inspection device further comprises an electronic memory and the database can be transferred to and/or stored in the memory.

16. The method of claim 12, wherein the reference database containing the reference data is obtained from the first indications in a session prior to the test operation, in a laboratory environment, with known ambient conditions, and the first calibration block is a standard calibration block.

* * * * *